United States Patent
Scheibe et al.

(10) Patent No.: US 9,149,607 B2
(45) Date of Patent: Oct. 6, 2015

(54) BI-DIRECTIONAL CATHETER STEERING HANDLE

(75) Inventors: Grant Scheibe, Loretto, MN (US);
Mark Nelson, Plymouth, MN (US);
Nick Kampa, Saint Paul, MN (US);
Aaron Opbroek, Brooklyn Park, NY (US); Tom Walch, Centerville, MN (US)

(73) Assignee: Greatbatch Ltd., Clarence, NY (US)

( * ) Notice: Subject to any disclaimer, the term of this patent is extended or adjusted under 35 U.S.C. 154(b) by 994 days.

(21) Appl. No.: 13/269,858

(22) Filed: Oct. 10, 2011

(65) Prior Publication Data
US 2012/0089125 A1    Apr. 12, 2012

Related U.S. Application Data

(60) Provisional application No. 61/391,216, filed on Oct. 8, 2010.

(51) Int. Cl.
*A61M 25/00*     (2006.01)
*A61M 25/01*     (2006.01)
*A61B 1/005*     (2006.01)

(52) U.S. Cl.
CPC ....... *A61M 25/0136* (2013.01); *A61M 25/0147* (2013.01); *A61B 1/0052* (2013.01); *A61M 2025/015* (2013.01)

(58) Field of Classification Search
CPC ............... A61M 25/0136; A61M 25/0147; A61M 2025/0161; A61M 25/0144; A61B 2018/00916; A61B 2018/00946; A61B 2018/00952

USPC .......... 604/523, 528, 264, 525, 95.01, 95.04, 604/170.03, 529; 600/585, 146
See application file for complete search history.

(56) References Cited

U.S. PATENT DOCUMENTS

| | | | |
|---|---|---|---|
| 5,489,270 A * | 2/1996 | van Erp | 604/95.04 |
| 5,571,085 A | 11/1996 | Accisano, III | |
| 5,944,690 A | 8/1999 | Falwell et al. | |
| 7,524,301 B2 | 4/2009 | Dubois et al. | |
| 7,691,095 B2 | 4/2010 | Bednarek et al. | |
| 2003/0109861 A1 | 6/2003 | Shimada | |
| 2006/0142694 A1* | 6/2006 | Bednarek et al. | 604/95.04 |
| 2007/0260223 A1 | 11/2007 | Scheibe et al. | |

(Continued)

FOREIGN PATENT DOCUMENTS

| | | |
|---|---|---|
| EP | 0904797 | 3/1999 |
| EP | 1676595 | 5/2006 |

(Continued)

OTHER PUBLICATIONS

European Search dated Jan. 5, 2012.

*Primary Examiner* — Bhisma Mehta
*Assistant Examiner* — Brandy S Lee
(74) *Attorney, Agent, or Firm* — Michael F. Scalise

(57) ABSTRACT

A deflectable sheath for use in medical procedures in the vasculature is described. The sheath includes a handle supporting the sheath. Two pull wires run along opposite sides of the sheath to anchors at the deflectable distal end. The handle includes a rotatable member that moves a threaded slider block in a back and forth translational manner. As that translational movement occurs, force is applied to either one or the other of the pull wires to cause deflection of distal end of the sheath in either and upwardly or a downwardly direction with respect to the longitudinal axis of the sheath.

18 Claims, 11 Drawing Sheets

(56) References Cited

U.S. PATENT DOCUMENTS

| | | |
|---|---|---|
| 2009/0281524 A1 | 11/2009 | Scheibe et al. |
| 2010/0004592 A1 | 1/2010 | Butler |
| 2010/0069834 A1 | 3/2010 | Schultz |
| 2010/0164137 A1 | 7/2010 | Selkee |

FOREIGN PATENT DOCUMENTS

| | | |
|---|---|---|
| EP | 1897581 | 12/2008 |
| WO | 0067834 | 11/2000 |

* cited by examiner

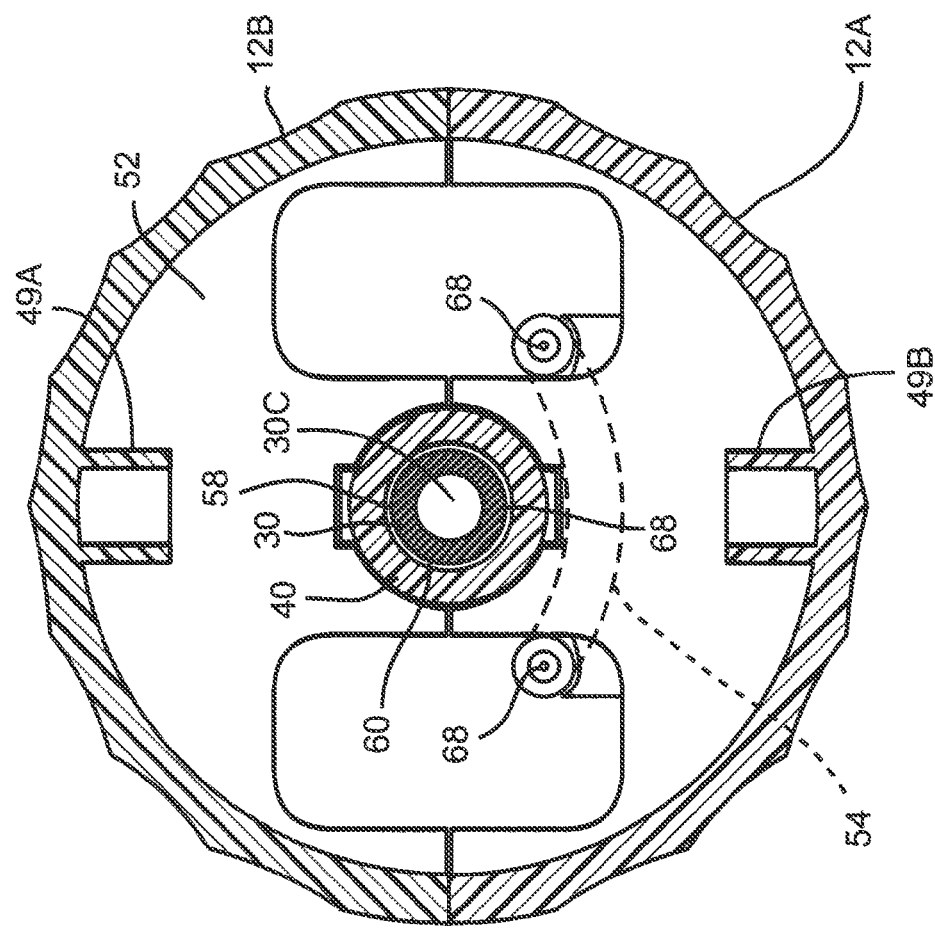

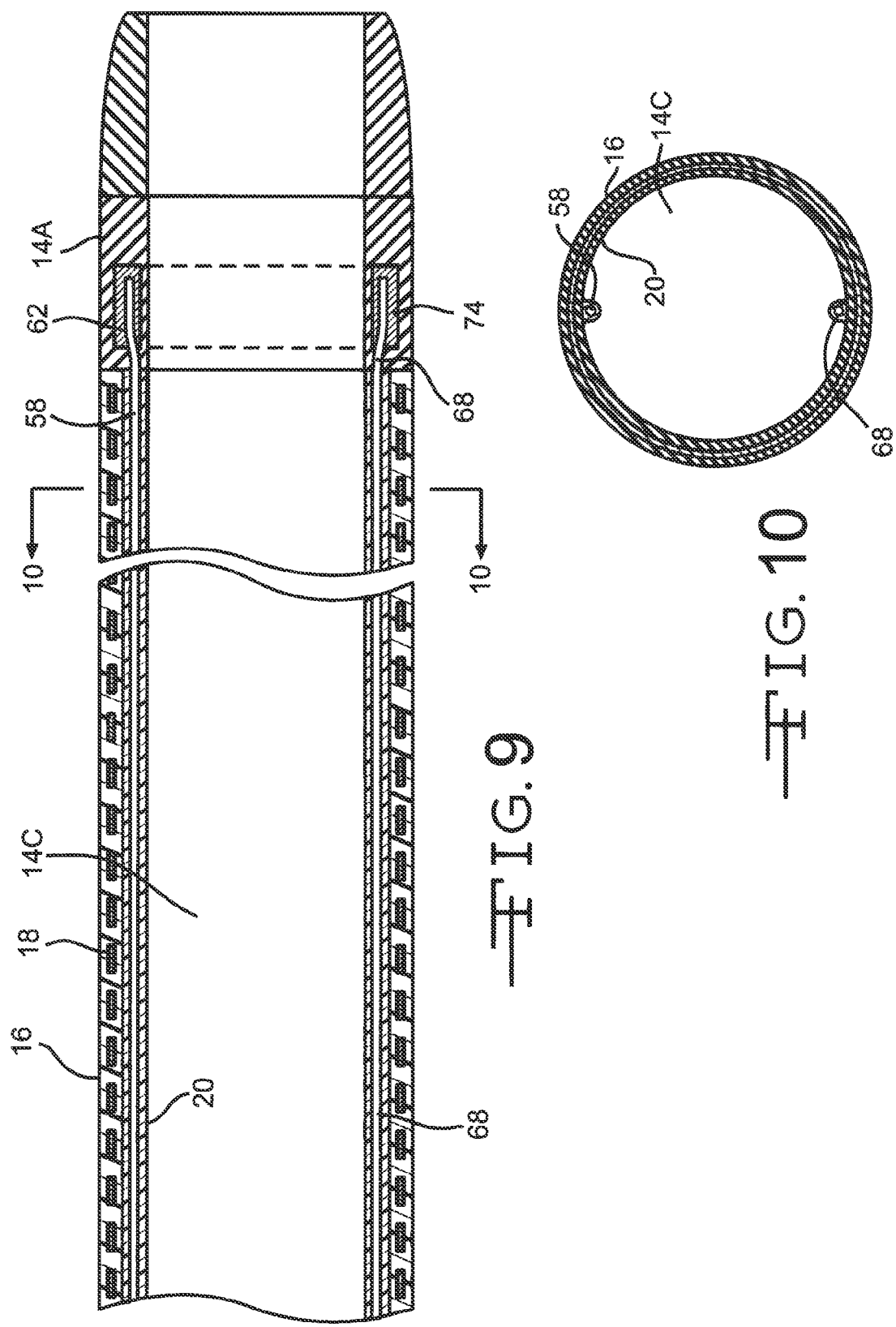

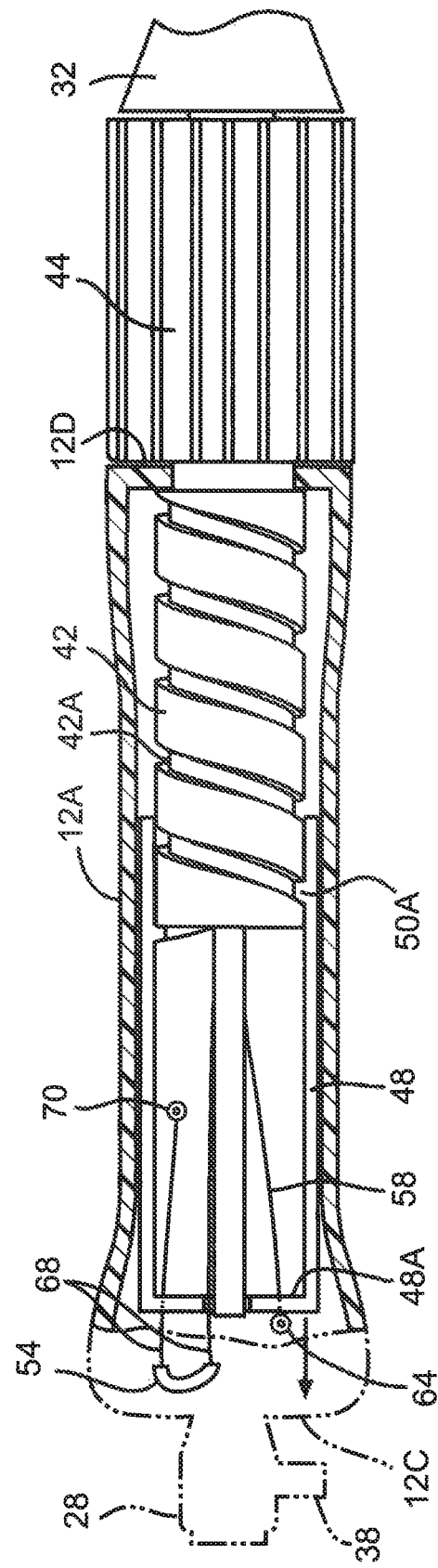

BI-DIRECTIONAL CATHETER STEERING HANDLE

CROSS-REFERENCE TO RELATED APPLICATION

This application claims priority from U.S. provisional Application Ser. No. 61/391,216, filed Oct. 8, 2010.

BACKGROUND OF THE INVENTION

The present invention generally relates to medical devices such as deflectable sheaths. More particularly, the present invention relates to a steering system for positioning the deflectable distal end of a catheter sheath in a desired orientation.

SUMMARY OF THE INVENTION

Many current deflectable catheters include a pull wire that extends from the distal end of the sheath to a deflection control actuator located in a handle. The pull wire may only be tensioned in one direction thereby providing for deflection in a single direction. Compression of the pull wire in another direction can buckle the wire. This substantially prevents active deflection of the sheath with the deflection control actuator in more than one direction. Straightening of the sheath in a direction opposed to that granted by tensioning the pull wire is thereby accomplished with the natural elasticity of the sheath distal end. The deflected sheath exerts a passive pulling force on the pull wire that straightens the sheath without active control through the deflection control actuator. Further, the elasticity of the sheath only straightens the distal end without providing for deflection of the sheath in an opposed direction.

What is needed is a deflectable sheath that overcomes the shortcomings of previous designs by providing for active deflection of the distal end in more than one direction or orientation.

SUMMARY OF THE INVENTION

The present invention relates to a novel design for a deflectable sheath for use in medical procedures, particularly where access to the vasculature is needed. The deflectable sheath comprises a tubular sheath providing a delivery lumen extending from a proximal portion to a deflectable distal sheath end. A handle is supported on the proximal sheath portion. First and second pull wires extend from the handle along the sheath to the deflectable distal sheath end. They are captured in a slidable relationship between the sheath and a liner except at the deflectable distal end of the sheath to which they are anchored. A threaded member is housed in the handle and threadingly mates to a slider block. That way, when a rotatable member of the handle is rotated, it causes the threaded member to rotate and translate the slider block in either a forwardly or backwardly direction along the handle.

A first pull wire extends from a first distal end anchored to the deflectable distal sheath end to a proximal first pull wire end provided with a first stop member located proximally of a rear wall of the slider block. A second pull wire extends from a second distal end at the deflectable distal sheath end and extends along the sheath and handle to a proximal second pull wire end provided with a second stop member located distally of the slider block. However, the second pull wire extends through a U-shaped tube located proximally of the slider block and the proximal end of the second pull wire. The U-shaped tube changes the direction and point of application of a pulling force applied to the second pull wire.

Then, when the rotatable member is manipulated in a first direction, the threaded member translates the slider block in a rearwardly direction against the first stop member to apply a first pulling force on the first pull wire. This force causes the distal sheath end to deflect into a first orientation out of alignment with respect to a longitudinal axis of the sheath. On the other hand, when the rotatable member is manipulated in a second direction, opposite the first direction, the threaded member translates the slider block in a forwardly direction against the second stop member to apply a second pulling force on the second pull wire that is slidingly received in the U-shaped tube. This force causes the distal sheath end to deflect into a second orientation out of alignment with respect to the longitudinal axis of the sheath. The second deflection direction is generally opposite that of the first deflection direction.

The foregoing and additional advances and characterizing features of the present invention will become clearly apparent upon reading the ensuing description together with the included drawings wherein:

BRIEF DESCRIPTION OF THE DRAWINGS

FIG. 6 is a cross-sectional view taken along line 6-6 of FIG. 2.

FIG. 9 is a cross-sectional view taken along line 9-9 of FIG. 1.

FIG. 10 is a cross-sectional view taken along line 10-10 of FIG. 9.

FIG. 12 is a partly broken away cross-sectional view of the handle assembly 12 showing the slider block 48 moving in a proximal direction.

DETAILED DESCRIPTION OF THE PREFERRED EMBODIMENTS

Figure 1:
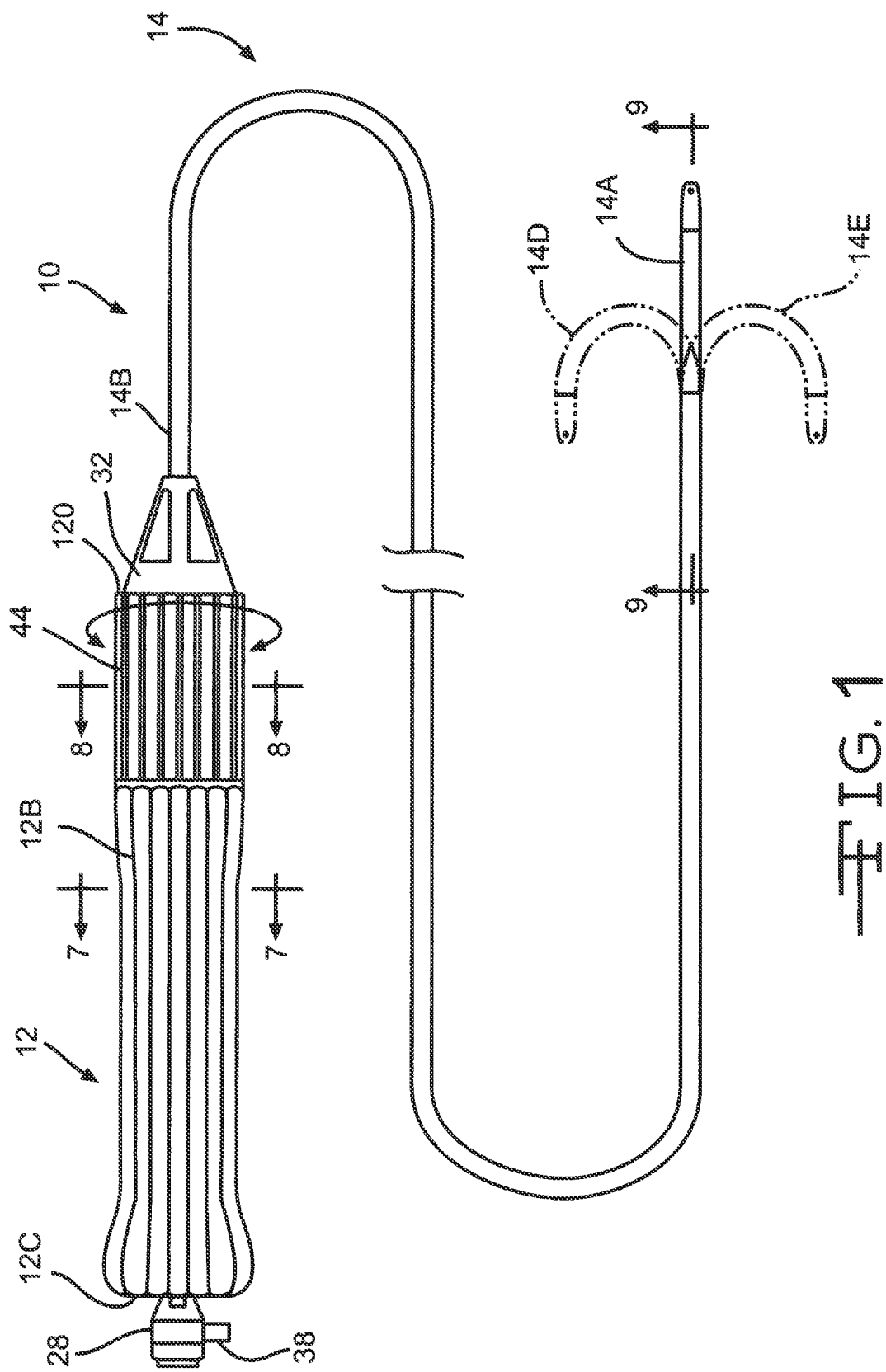
FIG. 1 is a perspective view of a bi-directional catheter assembly 10 according to the present invention.

Turning now to the drawings, FIG. 1 illustrates a bi-directional catheter assembly 10 according to the present invention. The bi-directional catheter assembly 10 comprises a handle assembly 12 supporting a deflectable sheath 14.

The deflectable sheath 14 comprises an elongate tubular structure that is flexible yet substantially non-compressible along its length. The deflectable sheath 14 extends from a deflectable distal end 14A (FIG. 1), which is adapted to be disposed within a patient, to a proximal portion 14B. The sheath 14 includes a delivery lumen 14C (FIGS. 9 and 10) that extends through the sheath body from the deflectable distal end 14A to the proximal portion 14B.

An exemplary construction, for the sheath 14 comprises an outer tubular member 16 formed of a polymeric material, such as of PEBAX, encasing a tubular braided wire 18 as a mesh. An inner liner 20 of a second polymeric material, for example PTFE, resides inside the outer PEBAX tube 16. The PTFE liner 20 provides the sheath lumen 14C with sufficient lubricity so that medical instruments, devices, and the like, slide through the sheath 14 with a minimal amount of force. The delivery lumen 14C is sized and shaped to receive, for example, instruments, fluids, media, and the like. The handle assembly 12, in turn, provides for selective deflection of the distal end 14A of the sheath 14 into anyone of a number of disparate orientations, as will be further described in detail herein below.

Figure 2:
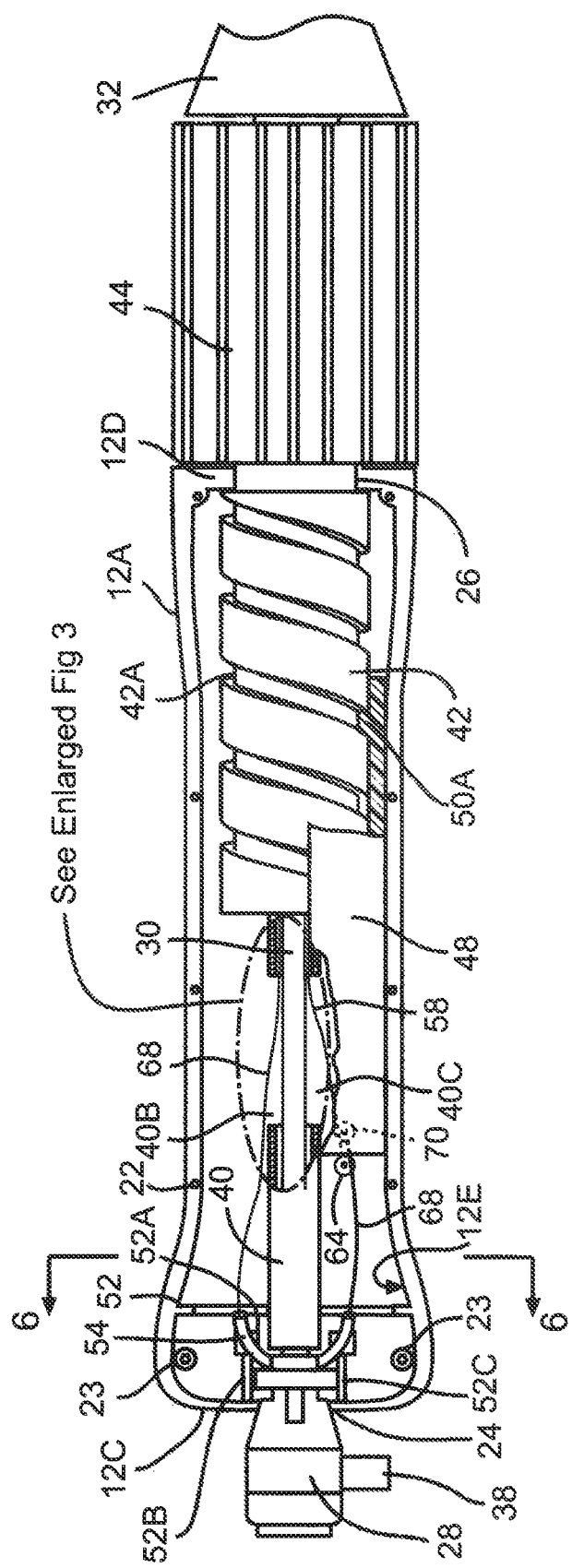
FIG. 2 is broken away and enlarged view of the handle assembly 12 for the catheter assembly 10.
Figure 4:
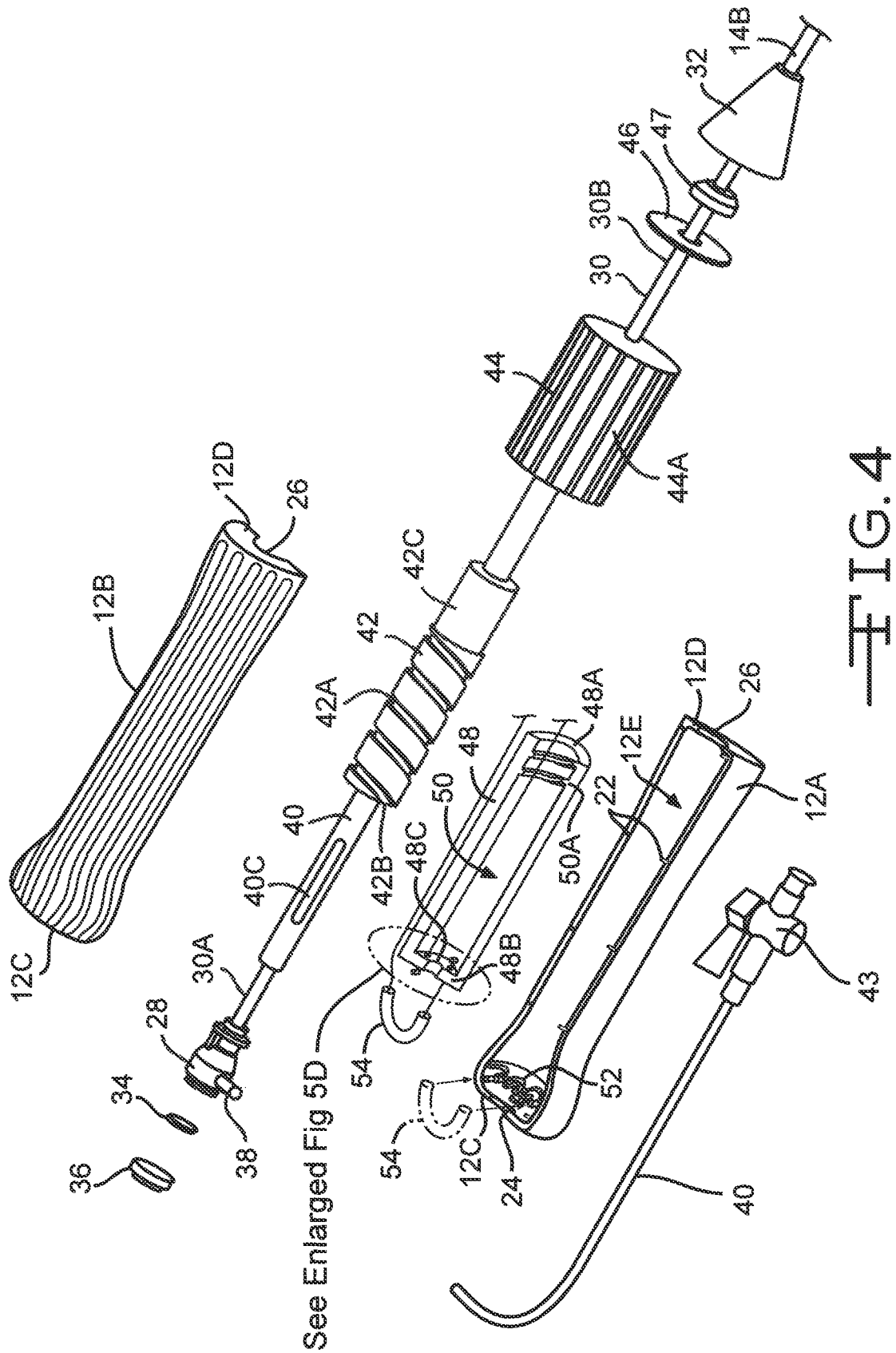
FIG. 4 is an exploded view of the handle assembly 12 of the bi-directional catheter 10 shown in FIG. 1.
Figure 7:
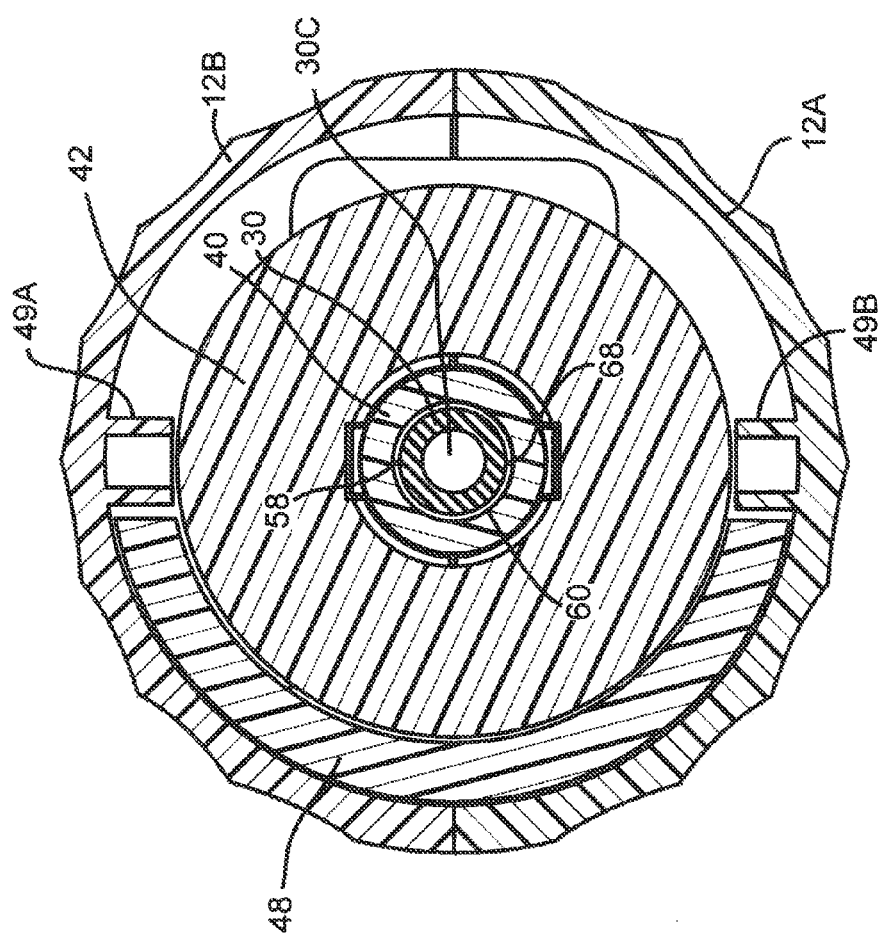
FIG. 7 is a cross-sectional view taken along line 7-7 of FIG. 1.
Figure 8:
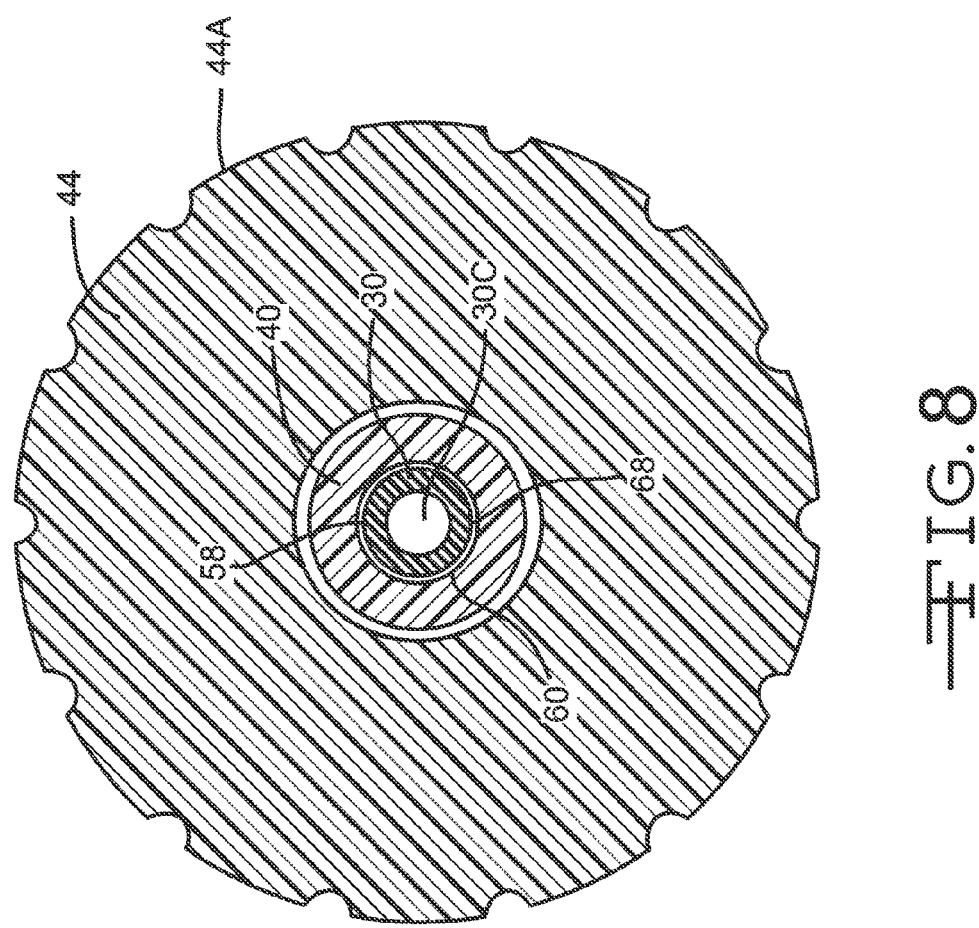
FIG. 8 is a cross-sectional view taken along line 8-8 FIG. 1.
Figure 11:
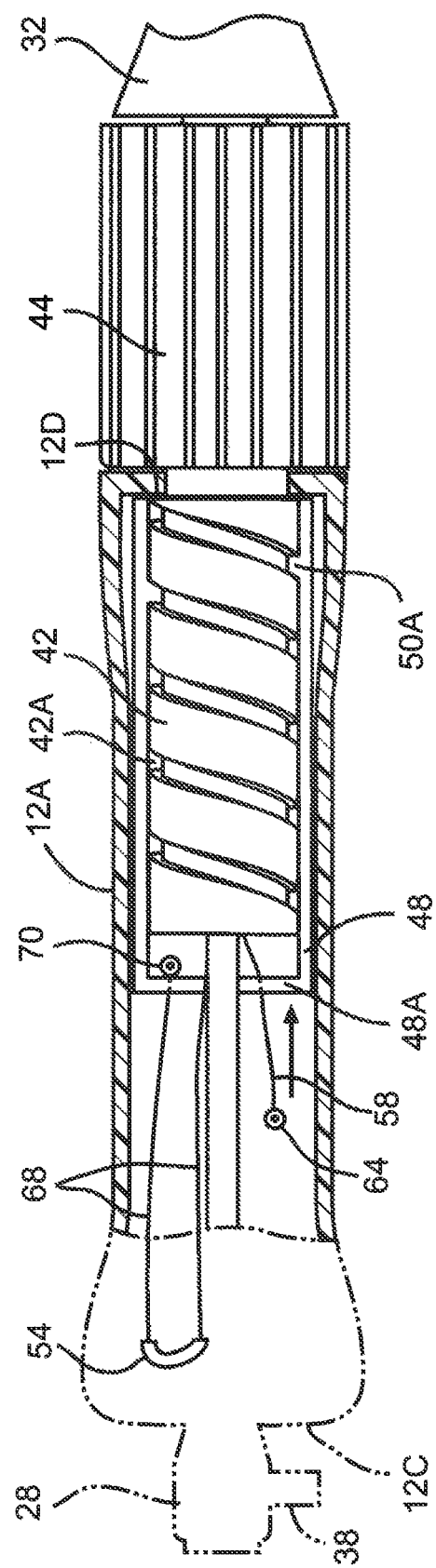
FIG. 11 is a partly broken away cross-sectional view of the handle assembly 12 showing the slider block 48 moving in a distal direction.

As shown in FIGS. 2, 4 and 7, the handle assembly 12 includes a lower handle portion 12A mated to an upper handle portion 12B. This mated relationship is effected by posts or protrusions 22 extending upwardly at spaced intervals along an edge of the lower handle portion 12A. The posts 22 are snap-fit into mating receptacles (not shown) on a corresponding edge of the upper handle portion 12B. Threaded openings 23 are also provided in the lower handle portion 12A. They receive threaded fasteners (not shown) to further help secure the handle portion 12A and 12B together.

As shown in FIGS. 2 and 4, the mated lower and upper handle portions 12A and 12B provide an ergonomically curved sidewall, the extent of which is defined by a handle proximal end wall 12C and a handle distal end wall 12D. The handle proximal end wall 12C includes a semi-circular opening 24. Likewise, the handle distal end wall 12D has a semi-circular opening 26 therein.

A hub 28 is over-molded onto the proximal end 30A of an elongate inner tube 30. The opposite, distal end 30B of the inner tube is received in a nose cone 32 where it connects to the proximal end 14B of the sheath 14 in an open communication manner.

The hub 28 has a tapered inner shape that serves to funnel and direct instruments and the like into a lumen 30C (FIGS. 6 to 9) provided through the tube 30 and in communication with the sheath lumen 14C. In that respect, the sheath 14 and inner tube 30 provide a sheath means with open communication from the hub 28 to and through the deflectable distal sheath end 14A. A sealable membrane 34 is seated against the proximal hub portion, captured there by a cap 36. The cap 36 has an annular groove (not shown) that snap-fits into engagement with an annular protrusion (not shown) on the outer wall of the hub 28.

A side port 38 exits through the wall of the hub 28. The side port 38 allows for introduction of fluids, such as saline or medicine, into and through the lumen 30C of the elongate tube 30 and into and through the sheath lumen 14C without having to remove instruments disposed through the tube and sheath lumens. A flexible tube 40 provided with a 3-way valve 43 is connected to the port 38 to facilitate selective introduction of fluids therein.

Figure 3:
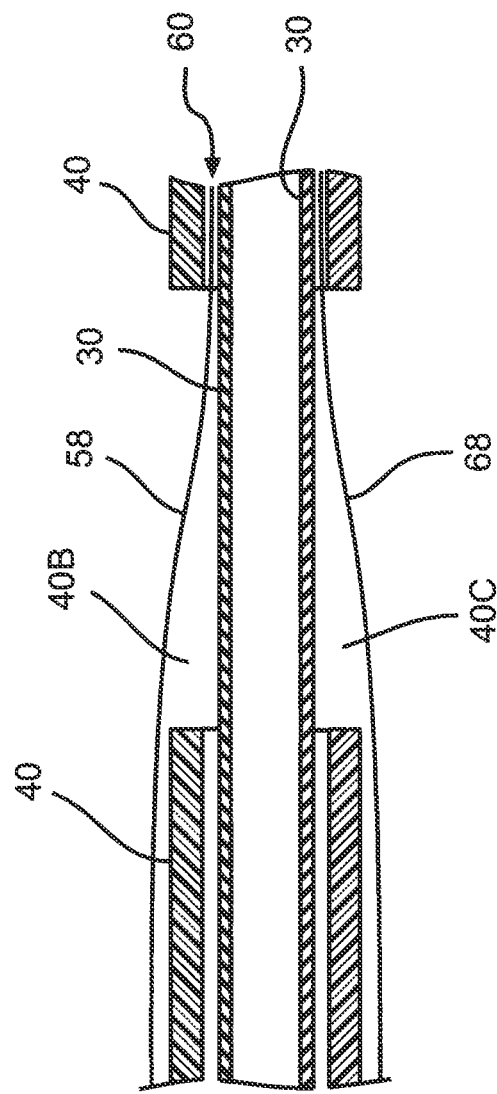
FIG. 3 is an enlarged view of the indicated area in FIG. 2.

As shown in FIG. 4, the elongate inner tube 30 supports an outer anchor rod 40 as a tubular structure that is somewhat shorter in length than the inner tube. The outer anchor rod 40, in turn, supports a threaded screw 42 that is connected to a distal thumb wheel 44. A pair of diametrically opposed axially aligned slots 40B, 40C (FIGS. 2 to 4) extend through the wall thickness of the outer anchor rod 40 at a position proximal to the threaded screw 42. The threaded screw 42 is provided with thread grooves 42A extending distally from the proximal end 42B along a majority of its length, but ending short of an unthreaded distal portion 42C thereof.

The thumb wheel 44 and the threaded screw 42 are connected together as a unitary construction. Consequently, rotational movement of the thumb wheel 44 causes the threaded screw 42 to rotate in a similar direction and at a similar rate. Axially aligned ridges 44A are spaced radially about the periphery of the thumb wheel 44. The ridges 44A serve as gripping surfaces to provide a physician using the present catheter 10 with better tactile feel. A washer 46 resides on the inner tube 30. An abutment nose 47 is mounted on the inner tube 30 intermediate the washer 46 and the nose cone 32.

As shown in FIGS. 2, 4, 7, 11 and 12 a slider block 48 is translationally supported on an inner surface 12E of the lower and upper handle portions 12A, 12B. The slider block 48 is confined in this position by opposed abutments 49A, 49B. That way, the slider block 48 is translationally or axially, but not rotationally, movable along the handle 12.

The slider block 48 has a U-shaped cross-section extending from an open distal end 48A to a wall 48B at its proximal end. The proximal wall 48B is provided with a curved inlet 48C sized to permit the anchor rod 48 and inner tube 30 to rest therein. An inner surface 50 of the slider block 48 is provided with at least one thread protrusion 50A. The threaded protrusion 50A has a height and shape that matches the depth and pitch of the threaded grooves 42A of the threaded member 42.

Figure 5C:
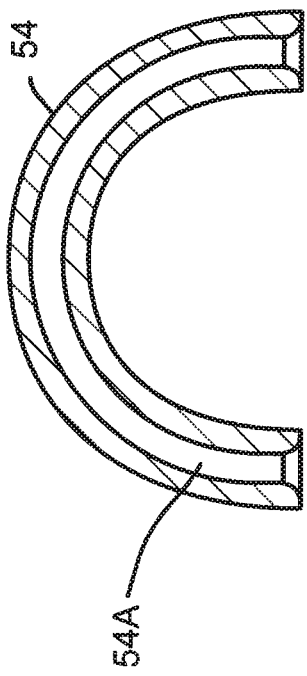
FIG. 5C is a cross-sectional view taken along line 5C-5C of FIG. 5B.

As shown in FIG. 2, the lower handle portion 12A is provided with an internal wall 52 aligned perpendicular to the longitudinal axis of the handle 12 and positioned adjacent to the proximal semi-circular opening 24. The internal wall 52 supports a proximally extending protrusion 52A spaced inwardly from upper and lower stepped webs 52B, 52C. The inner wall 52 in conjunction with the protrusion 52A and stepped webs 52B, 52C define a space that retains a U-shaped tube 54 therein (FIGS. 5A to 5C).

Figure 5D:
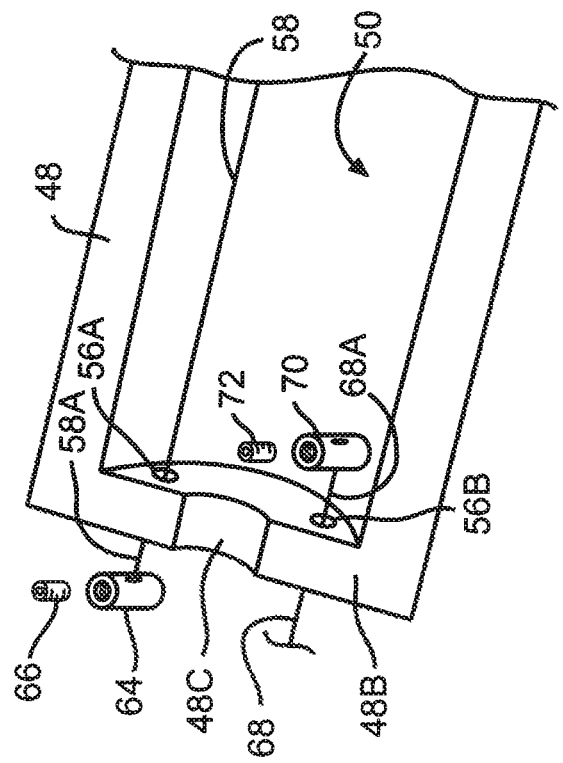
FIG. 5D is an enlarged view of the indicated area in FIG. 4.
Figure 5A:
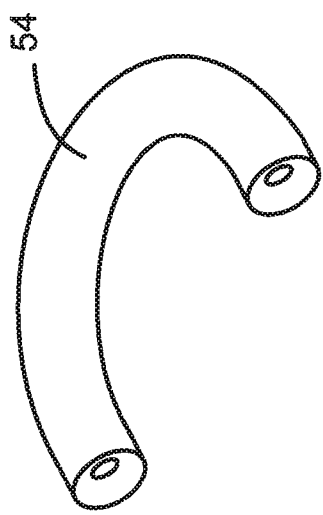
FIG. 5A is an enlarged view of the U-shaped hypo-tube of the handle assembly 12 shown in FIG. 4.
Figure 5B:
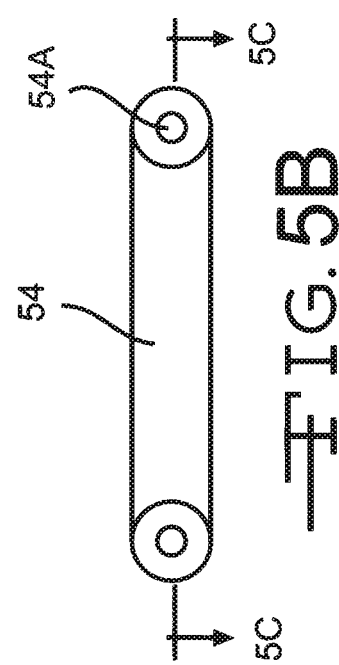
FIG. 5B is an end view of the hypo-tube 54 shown in FIG. 5A.

Referring now to FIG. 5D, the proximal wall 48B of the slider block 48 is provided with spaced apart openings 56A and 56B through the thickness thereof and aligned parallel to the longitudinal axis of the slider block and the handle 12. The openings 56A and 56B are provided on either side of curved inlet 48C.

A first pull wire 58 extends through the first opening 56A and along a portion of the length of the slider block 48 until it enters inlet slot 40B provided through the wall thickness of the outer anchor rod 40. From there, the first pull wire 58 extends along an annulus 60 formed between the outer surface of the inner tube 30 and the inner surface of the anchor rod 40 and then between the outer tubular member 16 and the inner liner 20 of the sheath 14. The first pull wire 58 terminates in an anchor 62 provided in the deflectable distal end 14A of the sheath. The opposite, proximal end 58A of the first pull wire 58 is received, in a first anchor pin 64, serving as a first stop member, and held in place by set screw 66. The first anchor pin 64 abuts against a proximal surface of the proximal slider block wall 48B.

The proximal end 68A of a second pull wire 68 is received in a second anchor pin 70, serving as a second stop member, and held in place by set screw 72. The second anchor pin 70 abuts against a distal surface of the proximal slider block wall 48B, opposite the proximal surface thereof against which the first anchor pin 64 abuts. From the second anchor pin 70, the second pull wire 68 extends through the second opening 56B in the proximal slider block wall 48B and through a lumen 54A provided by the U-shaped tube 54 nested in the lower handle portion 12A between the protrusion 52A and the opposed stepped webs 52B, 52C extending from the inner wall 52. From the U-shaped tube 54, the second pull wire 68 extends along a portion of the length of the slide block 48 until it enters inlet slot 40C provided through the thickness of the outer anchor rod 40. The hypo-tube 54 changes the direction and point of application of a pulling force applied to the second pull wire 68, as will be described in detail herein after. From there, the second pull wire 68 extends along the annulus 60 between the outer surface of the inner tube 30 and the inner surface of the anchor rod 40 and then between the outer tubular member 16 and the inner liner 20 of the sheath 14. The second pull wire 68 terminates in an anchor 74 provided in the deflectable distal end 14A of the sheath, opposite the first pull wire 58 and its terminus anchor 62. The first and second pull wires 58, 68 can be made of such disparate materials as stainless steel, NITINOL®, or flexible polymers and textile materials such as VECTRAN® or Spectra.

The U-shaped tube 54 is an improvement over the prior art where pulleys, posts, and the like are used as change-of-direction structures. These conventional structures do not confine and contain the pull wire as it travels back and forth across the pulley or post. That is not the case with the present U-shaped tube 54, which confines and contains the pull wire 68 therein. Furthermore, the U-shaped tube 54 is of a relatively lubricious polymeric material that promotes low friction movement of the pull wire 68 against its inner surface.

For a more detailed description of anchoring structures that are suitable for anchoring pull wires in deflectable sheath assemblies, reference is made to U.S. patent application Ser. No. 12/479,193, filed on Jun. 5, 2009, now U.S. Pat. No. 8,056,307 to Honebrink at al. This patent is assigned to the assignee of the present invention and incorporated herein by reference.

In that respect, the first and second anchor pins 64, 70 secured to the ends of the first and second pull wires 58, 68 serve as stops for their respective pull wires. As will be described in detail hereinafter, pulling forces imparted to the wires 58, 68 by manipulation of the rotatable knob 44 of the handle assembly 12 are transmitted by one or the other of the pull wires 58, 68 to the deflectable distal end 14A of the sheath 14 to cause deflection thereof in an intended manner.

In use, a physician inserts the distal end 14A of the sheath 14 into the vasculature of a patient. As shown in FIG. 1, the present bi-directional sheath assembly 10 provides for deflectable movement of the distal end 14A through a wide range both above and below a longitudinal axis defines by the longitudinal axis of the sheath distal end 14A. This deflectional motion is affected by rotational movement of the rotatable knob 44 in either a clockwise or counter clockwise direction.

Referring first to FIG. 2, this drawing shows the position of the slider block 48 with respect to the first and second anchor pins 64 and 70 secured to the proximal ends of the respective pull wires 58, 68. This represents a neutral position with the opposed first and second anchor pins 64, 70 at rest against the respective proximal and distal surfaces of the proximal slider block wall 48B. In this neutral position, the deflectable distal end 14A of the sheath is in a generally horizontal position, neither deflecting upwardly or downwardly, but aligned along the longitudinal axis of the sheath distal end.

As shown in FIG. 1, if it is desired to deflect the distal sheath end 14A in an upwardly direction, as shown by the upwardly extending dashed lines 14D in FIG. 1, the knob 44 is rotated in a clockwise direction. This causes the slider block 48 threadingly engaged with the threaded screw 42 to translate along the lower handle portion 12A in a forward direction towards the distal end 12D of the handle 12. As the slider block 48 translates forwardly, the second anchor pin 70 contacting the distal surface of the proximal slider block wall 48A causes the adjacent portion of the second pull wire 68 to move in a forwardly direction out from the lumen 54A of the hypo-tube 54. The remainder of the second pull wire moves in a rearwardly direction into the hypo-tube lumen 54A. As this occurs, force is transferred to the distal end of the pull wire 68 and its distal anchor 74 (FIG. 9), thereby causing the distal end 14A of the sheath 14 (FIG. 1) to deflect upwardly 14D. The first pull wire 58 does not move during this manipulation. Instead, it is stiff enough to maintain its "at rest" shape shown in FIG. 9.

Rotation of the knob 44 in an opposite, counter clockwise direction releases pressure from the second anchor pin 70 as the threaded screw 42 rotates, causing the slider block 48 to begin moving in a proximal direction. Once the slider block 48 is back to the neutral position shown in FIG. 2, the distal sheath end 14A relaxes into its neutral, longitudinal orientation (FIG. 1), neither deflecting upwardly or downwardly.

As shown in FIG. 12, should the physician want the distal sheath end 14A to deflect in a downwardly direction 14E (FIG. 2), the knob 44 is rotated in a counter clockwise direction. This causes the slider block 48 threadingly engaged with the counter clockwise rotating threaded screw 42 to translate along the lower handle portion 12A in a rearward direction towards the proximal end 12C of the handle 12. As the slider block 48 translates rearwardly, the first anchor pin 64 secured to the proximal end of the first pull wire 58 and abutting against the proximal surface of the proximal slider block wall 48A moves in a rearwardly direction. As the first pull wire 58 moves rearwardly, tension exerted on the pull wire 58 causes the distal end 14A of the sheath 14 to deflect downwardly 14E (FIG. 1). The second pull wire 68 does not move during this manipulation. It is stiff enough to retain its generally straight position shown in FIG. 9.

Then, rotation of the knob 44 in an opposite, clockwise direction causes the threaded screw 42 to counter rotate and move the slider block 48 forwardly to releases pressure from the first anchor pin 64 so that the first pull wire 58 moves in a proximal direction. Once the slider block 48 is back to the neutral position shown in FIG. 2, the distal sheath end 14A again relaxes into a neutral, longitudinal orientation, nether deflecting upwardly or downwardly.

It should be noted that the pull wires 58, 68 are only secured to the deflectable sheath 14 at their respective distal anchors 62, 74. The remainder of their lengths reside between the outer tubular member 16 of the sheath and the previously described inner liner 20 forming the sheath lumen 14C. In any event, there is a "space" between the sheath tubular member 16 and the liner 20 that permits movement of the pull wires there along. As is the case with the previously described U-shaped tube 54, the tubular sheath 16 and liner 20 are made of relatively lubricious polymeric materials that promote low friction movement of the pull wire 58 and 68 along the space there between.

Thus, it can be seen that the present invention provides a physician with a sheath assembly 10 that is capable of readily deflecting the distal sheath end 14A in any one of a myriad of directions, both upwardly and downwardly with respect to a longitudinal axis thereof. This provides the physician with a great degree of flexibility in maneuvering the distal end 14A of the sheath for performing a medical procedure inside the vasculature of a patient. Not only that, but the translational movement of the slider block 48 in a backward and forward direction to effect deflection movement of the sheath distal end 14A is built into a handle assembly 12 having a relatively compact size. This is a desirable attribute of the present bi-directional catheter 10 as the handle 12 fits nicely into the physician's palm to provide good tactile feel for sure and steady movement of the sheath distal end 14A.

It is appreciated that various modifications to the inventive concepts described herein may be apparent to those of ordinary skill in the art without departing from the spirit and scope of the present invention as defined by the appended claims.

What is claimed is:

1. A deflectable catheter, which comprises:
    a) a tubular sheath providing a delivery lumen extending from a proximal sheath portion to a deflectable distal sheath end;
    b) a handle supporting the proximal sheath portion;
    c) a longitudinal inner tube supported by the handle, the inner tube comprising an inner tube lumen extending from a distal inner tube end in open communication with the delivery lumen of the sheath to a proximal inner tube end located at a proximal end of the handle;
    d) a rotatable threaded member supported on an outer tubular rod housed inside the handle, wherein the inner tube extends through the outer tubular rod;
    e) a slider block housed inside the handle and comprising at least one thread that mates with the threaded member so that a rotational force imparted to the threaded member results in selected translational, but not rotational, movement of the slider block back-and-forth along the handle;
    f) first and second pull wires extending from the deflectable distal sheath end to the handle;
    g) wherein the first pull wire has a first distal end at the deflectable distal sheath end and extends through an annulus between the inner tube and the outer tubular rod supporting the threaded member with a proximal end of the first pull wire bearing against a proximal surface of a proximal end wall of the slider block housed inside the handle;
    h) wherein the second pull wire has a second distal end at the deflectable distal sheath end and extends through the annulus to a proximal U-shaped tube as a change-of-direction device and then to a proximal end of the second pull wire bearing against a distal surface of the proximal end wall of the slider block housed inside the handle;
    i) wherein the rotatable member is manipulatable in a first direction to translate the slider block in a rearwardly direction along the handle to apply a first pulling force on the first pull wire to thereby deflect the distal sheath end into a first orientation out of alignment, with respect to a longitudinal axis of the sheath; and
    j) wherein the rotatable member is manipulatable in a second direction, opposite the first direction, to translate the slider block in a forwardly direction to apply a second pulling force on the second pull wire to thereby deflect the distal sheath end into a second orientation out of alignment with respect to the longitudinal axis of the sheath.

2. The deflectable catheter of claim 1 wherein the proximal wall of the slider block comprises a first bore slidingly receiving the first pull wire and a second bore slidingly receiving the second pull wire.

3. The deflectable catheter of claim 1 wherein diametrically opposed slots are provided in a proximal portion of the outer tubular rod with the first and second pull wires passing through the respective slots prior to their bearing relationships with the proximal end wall of the slide block.

4. The deflectable catheter of claim 3 wherein first and second pull wires pass through the annulus between the inner tube and the outer tubular rod prior to passing through the diametrically opposed slots of the outer tubular rod prior to their bearing relationships with the proximal end wall of the slide block.

5. The deflectable catheter of claim 1 wherein the first orientation of the deflected distal sheath end is substantially opposite the second orientation.

6. The deflectable catheter of claim 1 wherein at least a portion of the first and second pull wires resides between the tubular sheath and a liner.

7. The deflectable catheter of claim 1 wherein the first and second pull wires are provided with respective anchors secure to the sheath at the deflectable sheath end.

8. The deflectable catheter of claim 1 wherein the first and second pull wires reside on diametrically opposite sides of the tubular sheath.

9. The deflectable catheter of claim 1 wherein the first and second pull wires are in slidable relationships with respective bores in the wire guide retainer.

10. The deflectable catheter of claim 1 wherein the rotatable member comprises a plurality of ridges spaced about its periphery.

11. The deflectable catheter of claim 1 wherein the proximal inner tube end connects to a funnel-shaped hub.

12. The deflectable catheter of claim 11 wherein the hub supports a sealable membrane.

13. The deflectable sheath of claim 1 wherein the hub includes a side port.

14. A deflectable catheter, which comprises:
    a) a tubular sheath providing a delivery lumen extending from a proximal sheath portion to a deflectable distal sheath portion;
    b) a handle supporting the proximal sheath portion;
    c) a rotatable threaded member supported on a tubular rod housed inside the handle;
    d) a slider block housed inside the handle and comprising at least one thread that mates with the threaded member so that a rotational force imparted to the threaded member results in selected translational, but not rotational, movement of the slider block back-and-forth along the handle;
    e) first and second pull wires extending from the deflectable distal sheath end to the handle;
    f) wherein the first pull wire has a first distal end at the deflectable distal sheath end and extends to a proximal end of the first pull wire bearing against a proximal surface of a proximal end wall of the slider block housed inside the handle;
    g) wherein the second pull wire has a second distal end at the deflectable distal sheath end and extends to a proximal change-of-direction device where the second pull wire curves through a lumen to a proximal end of the second pull wire bearing against a distal surface of the proximal end wall of the slider block housed inside the handle;
    h) wherein the rotatable member is manipulatable in a first direction to translate the slider block in a rearwardly direction along the handle to apply a first pulling force on the first pull wire to thereby deflect the distal sheath end into a first orientation out of alignment with respect to a longitudinal axis of the sheath; and
    i) wherein the rotatable member is manipulatable in a second direction, opposite the first direction, to translate the slider block in a forwardly direction to apply a second pulling force on the second pull wire to thereby deflect the distal sheath end into a second orientation out of alignment with respect to the longitudinal axis of the sheath.

15. A method for providing a deflectable catheter, comprising the steps of:
   a) providing a tubular sheath having a delivery lumen extending from a proximal sheath portion to a deflectable distal sheath end;
   b) connected a handle to the proximal sheath portion;
   c) positioning a longitudinal inner tube in the handle, the inner tube comprising an inner tube lumen extending from a distal inner tube end in open communication with the delivery lumen of the sheath to a proximal inner tube end located at a proximal end of the handle;
   d) supporting a rotatable threaded member on an outer tubular rod housed inside the handle, wherein the inner tube extends through the outer tubular rod;
   e) housing a slider block supported inside the handle, the slider block comprising at least one thread that mates with the threaded member so that a rotational force imparted to the threaded member results in selected translational, but not rotational, movement of the slider block back-and-forth along the handle;
   f) providing first and second pull wires extending from the deflectable distal sheath end to the handle;
   g) wherein the first pull wire has a first distal end at the deflectable distal sheath end and extends through an annulus between the inner tube and the outer tubular rod supporting the threaded member with a proximal end of the first pull wire bearing against a proximal surface of a proximal end wall of the slider block housed inside the handle;
   h) wherein the second pull, wire has a second distal end at the deflectable distal sheath end and extends through the annulus to a proximal U-shaped tube as a change-of-direction device and then to a proximal end of the second pull wire bearing against a distal surface of the proximal end wall of the slider block housed inside the handle;
   i) manipulating the rotatable member in a first direction to translate the slider block in a rearwardly direction along the handle to apply a first pulling force on the first pull wire to thereby deflect the distal sheath end into a first orientation out of alignment with respect to a longitudinal axis of the sheath; and
   i) manipulating the rotatable member in a second direction, opposite the first direction, to translate the slider block in a forwardly direction to apply a second pulling force on the second pull wire to thereby deflect the distal sheath end into a second orientation out of alignment with respect to the longitudinal axis of the sheath.

16. The method of claim 15 including providing the proximal wall of the slider block comprising a first bore slidingly receiving the first pull wire and a second bore slidingly receiving the second pull wire.

17. The method of claim 15 including providing diametrically opposed slots in a proximal portion of the outer tubular rod with the first and second pull wires passing through the respective slots prior to their bearing relationships with the proximal end wall of the slide block.

18. The method of claim 17 including routing the first and second pull wires pass through an annulus between the inner tube and the outer tubular rod tubes prior to passing them through the diametrically opposed slots of the outer tubular rod prior to their bearing relationships with the proximal end wall of the slide block.

* * * * *

UNITED STATES PATENT AND TRADEMARK OFFICE
CERTIFICATE OF CORRECTION

PATENT NO. : 9,149,607 B2
APPLICATION NO. : 13/269858
DATED : October 6, 2015
INVENTOR(S) : Grant Scheibe et al.

Page 1 of 1

It is certified that error appears in the above-identified patent and that said Letters Patent is hereby corrected as shown below:

In the Claims

Column 7, line 47 (Claim 1, line 39) after the word "alignment" delete the ","

Column 9, line 6 (Claim 15, line 6) delete "connected" and insert --connecting--

Signed and Sealed this
Twenty-eighth Day of June, 2016

Michelle K. Lee
*Director of the United States Patent and Trademark Office*